(12) United States Patent
Kamiya et al.

(10) Patent No.: US 8,615,069 B2
(45) Date of Patent: Dec. 24, 2013

(54) ACCOMMODATING CASE AND DEVICE SYSTEM

(75) Inventors: Takeshi Kamiya, Kanagawa (JP); Yasunori Ohta, Kanagawa (JP); Yusuke Kitagawa, Kanagawa (JP); Haruyasu Nakatsugawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 225 days.

(21) Appl. No.: 13/064,924

(22) Filed: Apr. 26, 2011

(65) Prior Publication Data

US 2011/0261516 A1    Oct. 27, 2011

(30) Foreign Application Priority Data

Apr. 27, 2010 (JP) .................... 2010-102451

(51) Int. Cl.
*H05G 1/10* (2006.01)
*H05G 1/06* (2006.01)
*H05G 1/02* (2006.01)
*H05G 1/00* (2006.01)

(52) U.S. Cl.
USPC ........... 378/102; 378/103; 378/197; 378/204; 378/210

(58) Field of Classification Search
USPC ............... 378/91, 98, 98.8, 101–103, 189, 378/193–198, 204, 210
See application file for complete search history.

(56) References Cited

U.S. PATENT DOCUMENTS

| 6,169,384 B1* | 1/2001 | Shannon ................ 320/107 |
| 6,169,782 B1* | 1/2001 | Zetterlund ............. 378/103 |
| 7,359,482 B2* | 4/2008 | Schmitt ................. 378/98.8 |
| 7,394,165 B2* | 7/2008 | Schiller ................. 290/1 R |
| 2005/0276379 A1 | 12/2005 | Polichar et al. |
| 2006/0032687 A1* | 2/2006 | Park et al. ................ 180/206 |
| 2007/0133751 A1 | 6/2007 | Chicchetti et al. |
| 2008/0036417 A1 | 2/2008 | Toya et al. |
| 2008/0240358 A1* | 10/2008 | Utschig et al. ........... 378/107 |
| 2009/0028295 A1 | 1/2009 | Ohta et al. |
| 2010/0054399 A1 | 3/2010 | Nishino et al. |

FOREIGN PATENT DOCUMENTS

| DE | 19729434 A1 | 2/1999 |
| JP | 2001-309562 A | 11/2001 |
| JP | 2008-048473 A | 2/2008 |
| JP | 2008-170315 A | 7/2008 |

(Continued)

OTHER PUBLICATIONS

Office Action issued by EPO on Aug. 8, 2013, in connection with corresponding European Patent Application No. 11163705.4.

(Continued)

*Primary Examiner* — Anastasia Midkiff
(74) *Attorney, Agent, or Firm* — Jean C. Edwards; Edwards Neils PLLC

(57) ABSTRACT

A portable radiographic imaging device and a portable X-ray source, that operate due to a first and second rechargeable battery respectively, can be accommodated in an accommodating case that is portable. While the accommodating case is being transported, a charging circuit provided in the accommodating case acquires electric power from a third rechargeable battery accommodated in the accommodating case, and charges the first and second rechargeable batteries. In this way, by accommodating the portable radiographic imaging device and the portable X-ray source in the accommodating case, the rechargeable batteries for the portable radiographic imaging device and the portable X-ray source are charged during transport.

6 Claims, 10 Drawing Sheets

(56) References Cited

FOREIGN PATENT DOCUMENTS

| | | |
|---|---|---|
| JP | 2008-206219 A | 9/2008 |
| JP | 2010-16977 | 1/2010 |
| JP | 2010-051477 A | 3/2010 |

OTHER PUBLICATIONS

Notice of Reasons for Rejection issued by the JPO on Sep. 17, 2013, in connection with corresponding Japanese Patent Application No. 2010-102451.

* cited by examiner

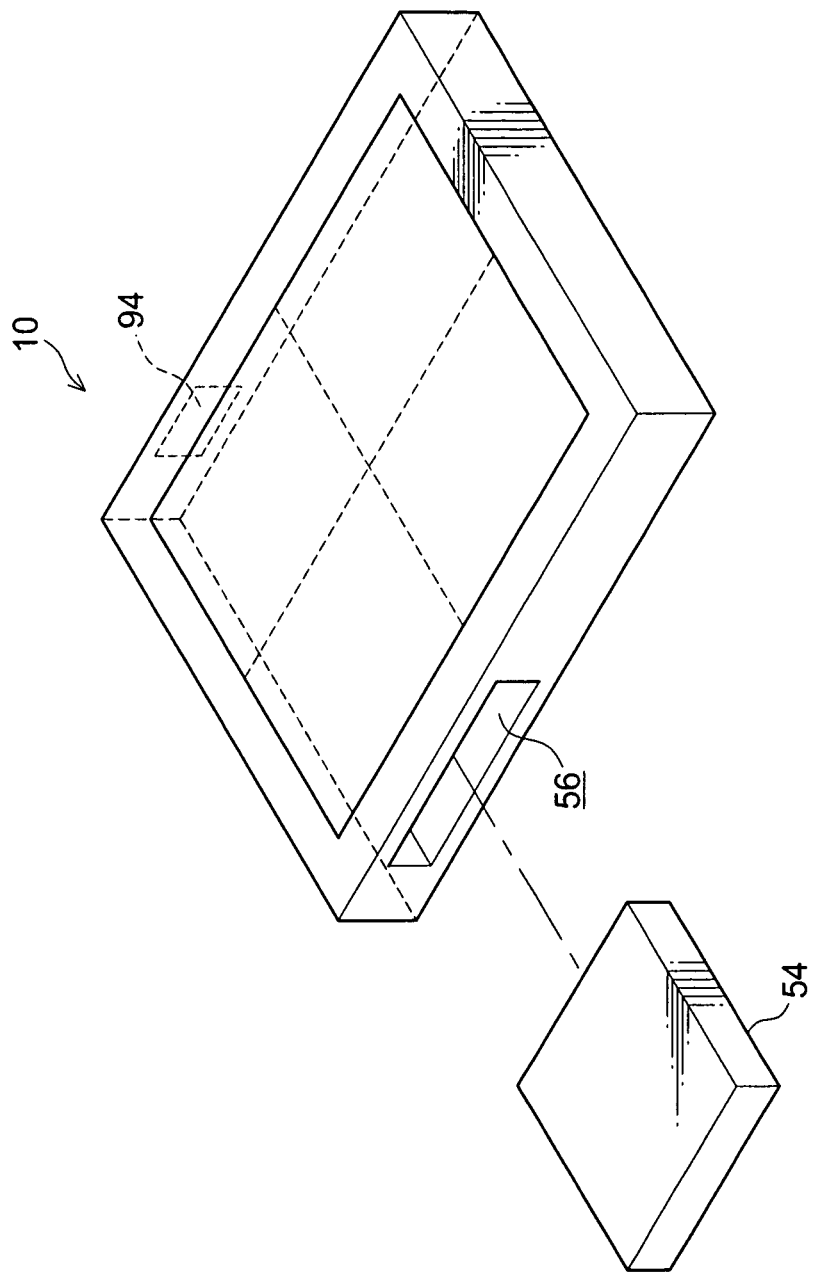

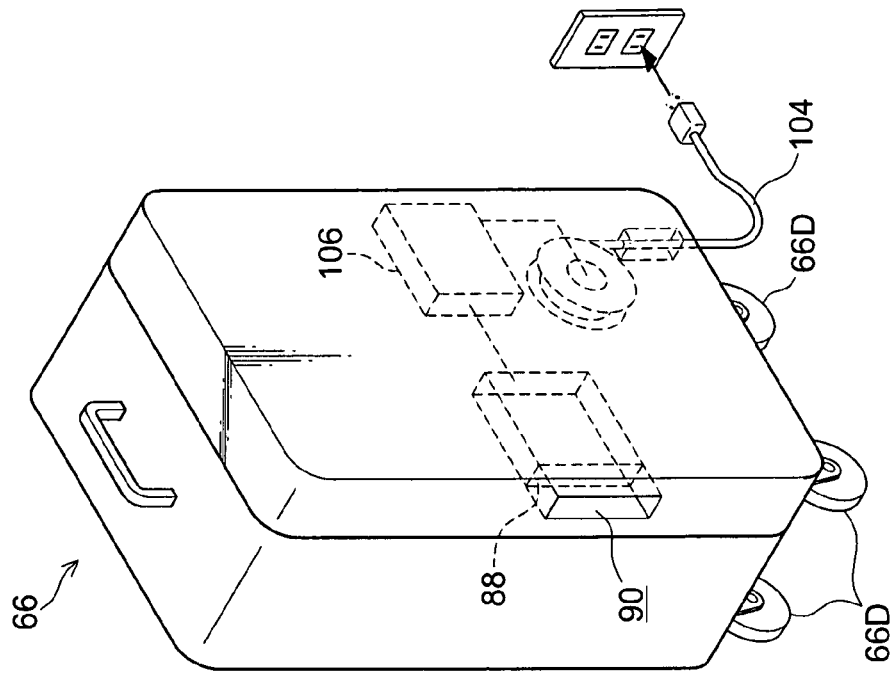
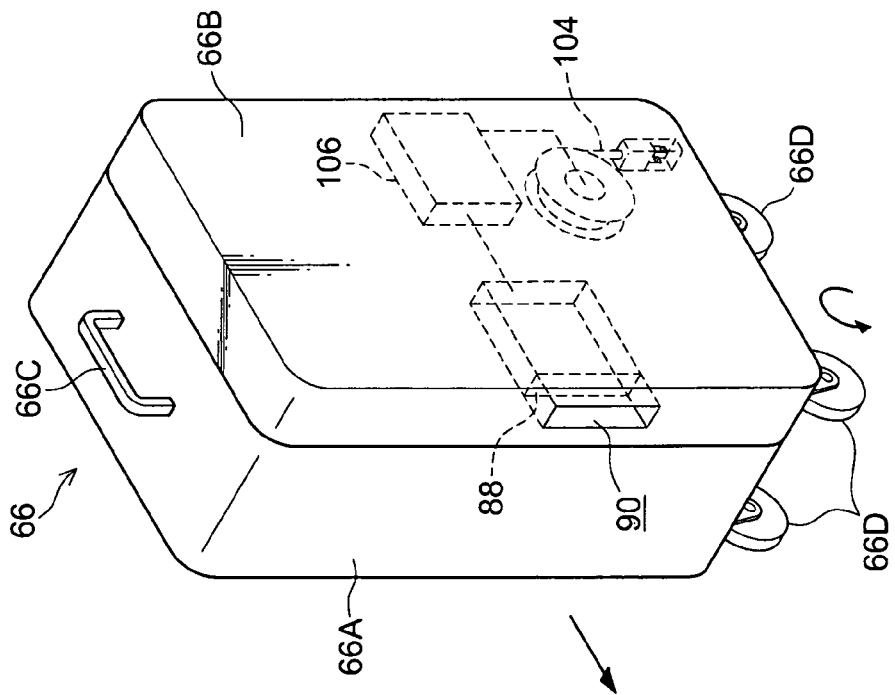

ACCOMMODATING CASE AND DEVICE SYSTEM

CROSS-REFERENCE TO RELATED APPLICATION

This application claims priority under 35 USC 119 from Japanese Patent Application No. 2010-102451, filed on Apr. 27, 2010, the disclosure of which is incorporated by reference herein.

BACKGROUND OF THE INVENTION

1. Field of the Invention

The present invention relates to an accommodating case that has an accommodating portion that can accommodate at least one of a portable radiographic imaging device and a portable X-ray source, and to a device system.

2. Description of the Related Art

Japanese Patent Application Laid-Open (JP-A) No. 2010-16977 discloses a portable radiographic imaging device (an electronic cassette). A handle portion is provided at this portable radiographic imaging device. By hooking the handle portion on a projecting portion that is provided, the handle portion and the projecting portion are electrically connected, and a rechargeable battery of the portable radiographic imaging device is charged through the handle portion.

However, in conventional techniques, when, due to imaging being carried out during a visit to an individual's home or a visit to a nursing facility or the like for example, the portable radiographic imaging device or the portable X-ray source is brought to the destination of the visit and used thereat, the rechargeable battery, that is provided in order to make the portable radiographic imaging device or the portable X-ray source operate, must be charged in advance. Further, there is also the problem that the rechargeable battery, that is provided at the portable radiographic imaging device or the portable X-ray source, discharges during transport.

SUMMARY OF THE INVENTION

The present invention makes it possible to, when bringing a portable radiographic imaging device or a portable X-ray source to a destination of a visit and using it thereat, charge, during transport, the rechargeable battery that makes the portable radiographic imaging device or the portable X-ray source operate.

A first aspect of the present invention is an accommodating case that is portable and has: an accommodating section that can accommodate at least one of a portable radiographic imaging device, that records radiographic images expressed by irradiated radiation and that operates due to a first rechargeable battery, and a portable X-ray source, that irradiates radiation toward the portable radiographic imaging device and operates due to a second rechargeable battery; and charging unit that acquires electric power from an electric power supplying source, and can charge at least one of the first rechargeable battery and the second rechargeable battery.

In accordance with the above-described structure, at least one of a portable radiographic imaging device and a portable X-ray source, that operate due to a first rechargeable battery or a second rechargeable battery, can be accommodated in the accommodating section of the accommodating case that is portable. Further, the charging unit provided at the accommodating case acquires electric power from an electric power supplying source, and can charge at least one of the first rechargeable battery and the second rechargeable battery.

In this way, by providing the charging unit at the accommodating case, at least one of the first rechargeable battery and the second rechargeable battery can be charged in a state in which at least one of the portable radiographic imaging device and the portable X-ray source is accommodated in the accommodating case that is portable.

In an accommodating case relating to a second aspect of the present invention, in the above-described first aspect, the electric power supplying source is a third rechargeable battery provided in the accommodating case, and a power source cable, that can charge the third rechargeable battery by electric power from an exterior, is provided.

In accordance with the above-described structure, the third rechargeable battery that serves as the electric power supplying source, and the power source cable that can charge the third rechargeable battery by electric power from the exterior, are provided at the accommodating case.

In this way, by providing the third rechargeable battery at the accommodating case, at least one of the first rechargeable battery and the second rechargeable battery can be charged by a simple structure during transport of the portable radiographic imaging device or the portable X-ray source.

Further, at the destination of a visit or in a hospital, the third rechargeable battery can be charged by connecting the power source cable to an outlet (e.g., a wall outlet) that can supply electric power.

Further, if the portable radiographic imaging device and the portable X-ray source are to be charged individually, cables provided at the portable radiographic imaging device and the portable X-ray source respectively must be connected to outlets that can supply electric power. Therefore, there may not be a sufficient number of insertion ports of the outlet. However, in the present invention, the third rechargeable battery, that is used to charge the first rechargeable battery and the second rechargeable battery, can be charged by inserting the power source cable, that is provided at the accommodating case, into an outlet. Therefore, the number of insertion ports of the outlet is not insufficient.

The insertion shapes of outlets differ in accordance with the country or geographical region, and differ also in accordance with the means of transport (planes, boats, automobiles and the like). Thus, if cables for charging are provided respectively at the portable radiographic imaging device and the portable X-ray source, cables suited to respective specifications are needed for both (in this case, two cables×countries or geographical regions, or means of transport). However, in the present invention, because the power source cable is provided at the accommodating case, the third rechargeable battery can be charged by making only the power source cable suit the respective specifications (one cable×countries or geographical regions, or means of transport).

An accommodating case relating to a third aspect of the present invention may be structured such that, in the above-described second aspect, a self-discharge rate of the third rechargeable battery is small as compared with the first rechargeable battery and the second rechargeable battery.

In accordance with the above-described structure, the self-discharge rate of the third rechargeable battery is small as compared with the first rechargeable battery and the second rechargeable battery. Therefore, when the third rechargeable battery is accommodated in the accommodating case and the first rechargeable battery and the second rechargeable battery are charged by using the third rechargeable battery, the first rechargeable battery and the second rechargeable battery can be charged effectively.

In an accommodating case relating to a fourth aspect of the present invention, in the above-described second or third aspect, the third rechargeable battery is provided so as to be able to be installed and removed.

In accordance with the above-described structure, the third rechargeable battery is provided so as to be able to be installed in and removed from the accommodating case. Therefore, while the portable radiographic imaging device and the portable X-ray source are accommodated in the accommodating case and transported, when the charged amount of the third rechargeable battery becomes low, the first rechargeable battery and the second rechargeable battery can be charged by replacing the installed third rechargeable battery with a charged third rechargeable battery that has been readied in advance.

In an accommodating case relating to a fifth aspect of the present invention, in any of the above-described first through fourth aspects, electricity receiving portions of the portable radiographic imaging device and the portable X-ray source accommodated in the accommodating section, and electricity supplying portions provided at the accommodating section, do not contact one another.

In accordance with the above-described aspect, the electricity receiving portions of the portable radiographic imaging device and the portable X-ray source that are accommodated in the accommodating section, and the electricity supplying portions that are provided at the accommodating section, do not contact one another. Therefore, the waterproofness and the appearance of the portable radiographic imaging device and the portable X-ray source can be improved.

A device system relating to a sixth aspect of the present invention has: the accommodating case of any of the above-described first through fifth aspects; and at least one of a portable radiographic imaging device and a portable X-ray source that is accommodated in the accommodating section provided at the accommodating case.

In accordance with the above-described structure, the accommodating case of any of the above-described first through fifth aspects is provided at the device system. Therefore, at least one of the first rechargeable battery and the second rechargeable battery can be charged in a state in which at least one of the portable radiographic imaging device and the portable X-ray source is accommodated in the accommodating case that is portable.

In accordance with the present invention, when bringing a portable radiographic imaging device or a portable X-ray source to a destination of a visit and using it thereat, the rechargeable battery, that makes the portable radiographic imaging device or the portable X-ray source operate, can be charged during transport.

BRIEF DESCRIPTION OF THE DRAWINGS

FIG. 3 is a perspective view showing a portable radiographic imaging device used in the device system relating to the first exemplary embodiment of the present invention;

FIGS. 4A and 4B are perspective views showing the accommodating case relating to the first exemplary embodiment of the present invention;

DETAILED DESCRIPTION OF THE INVENTION

Figure 1:
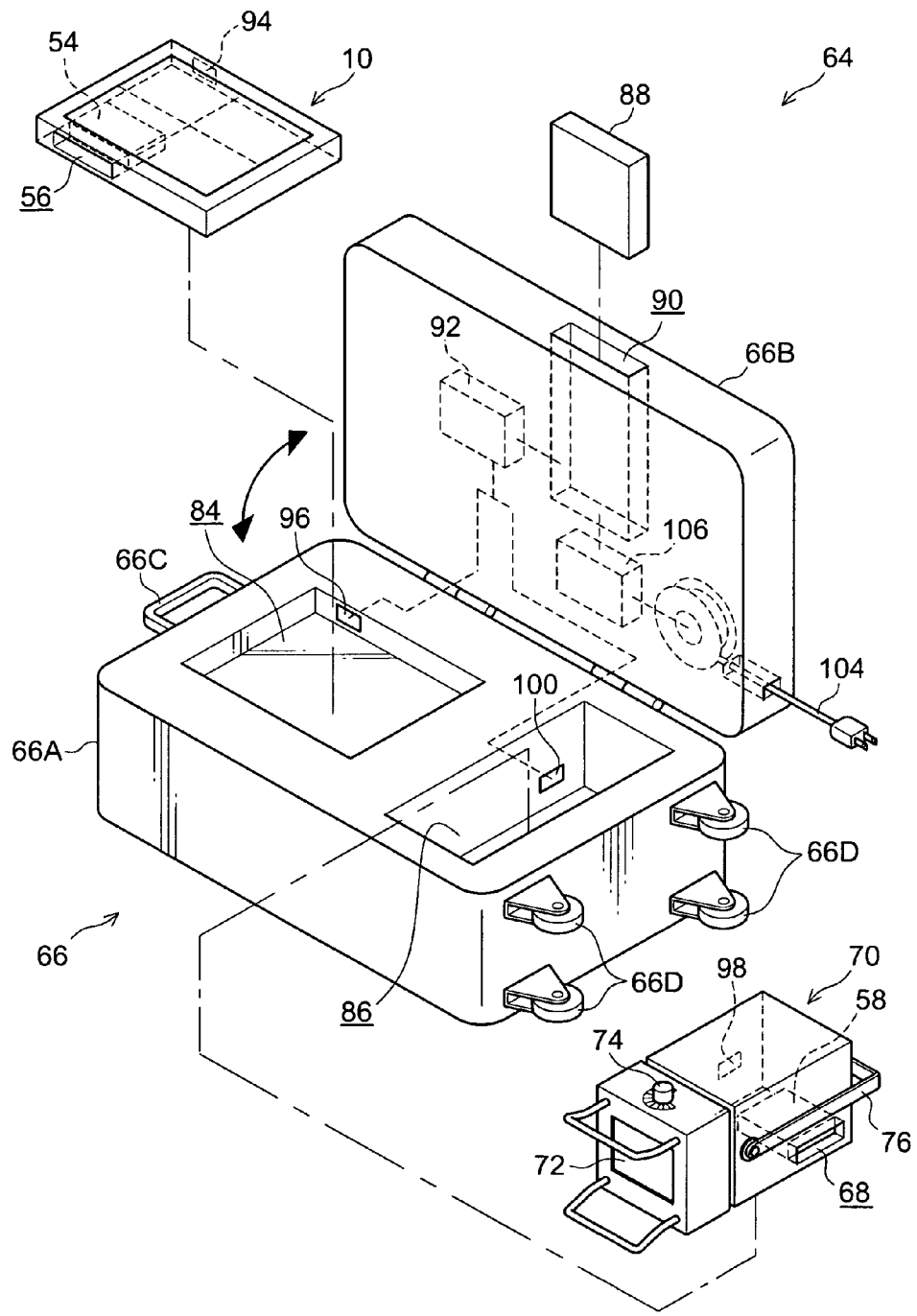
FIG. 1 is a perspective view showing an accommodating case and a device system relating to a first exemplary embodiment of the present invention.

Examples of an accommodating case 66 and a device system 64 relating to a first exemplary embodiment of the present invention are described in accordance with FIG. 1 through FIG. 8. Note that arrow UP in the drawings indicates upward in the vertical direction.

(Overall Structure)

Figure 6:
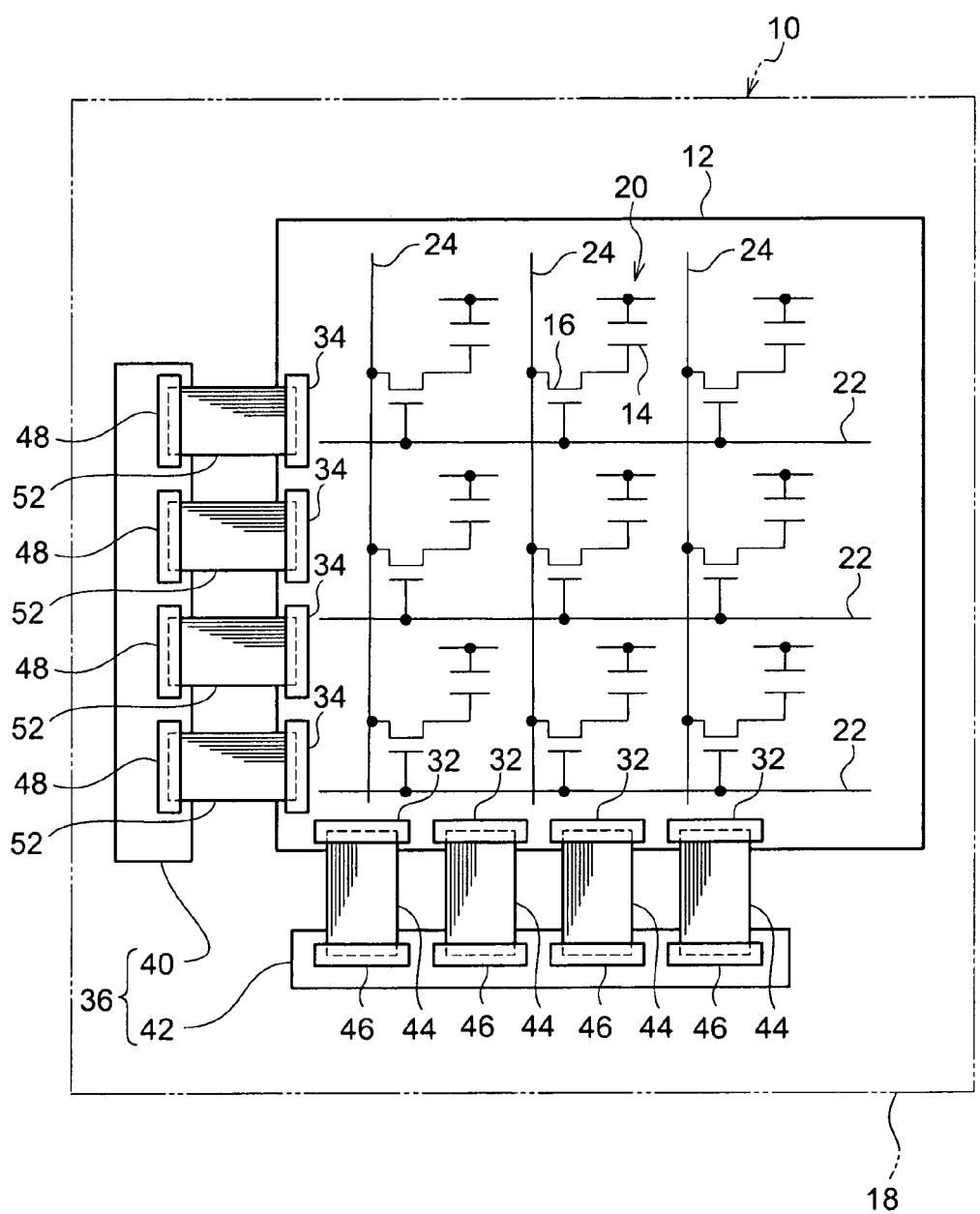
FIG. 6 is a circuit diagram showing the portable radiographic imaging device relating to the first exemplary embodiment of the present invention.
Figure 7:
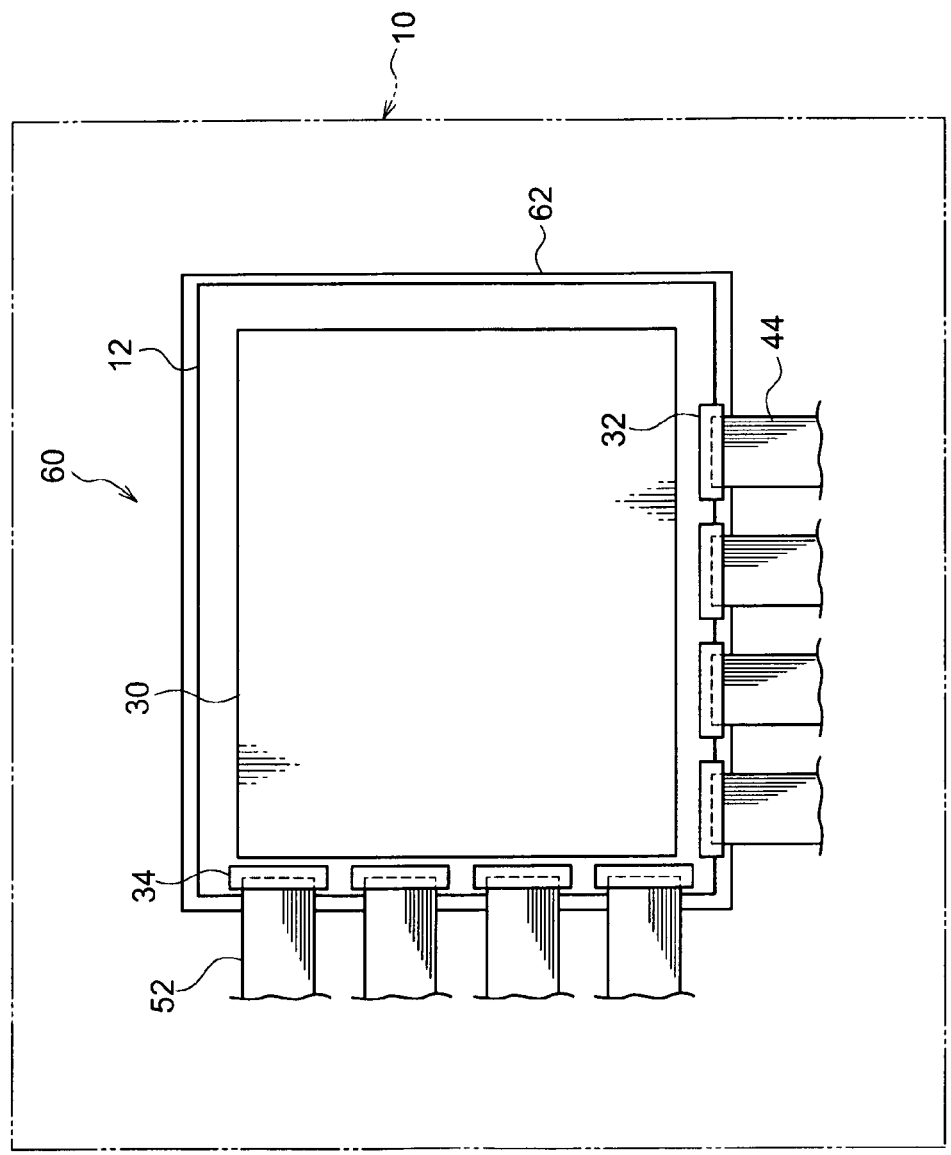
FIG. 7 is a plan view showing the portable radiographic imaging device relating to the first exemplary embodiment of the present invention.

As shown in FIG. 6, a radiographic imaging element 12 is provided within a housing 18 of a portable radiographic imaging device 10 (a so-called electronic cassette) that is provided at the device system 64 (see FIG. 1). The radiographic imaging element 12 has an upper electrode, a semiconductor layer, and a lower electrode. Numerous pixels 20, that are structured to include a sensor portion 14 that receives light and accumulates charges and a TFT switch 16 for reading-out the charges accumulated in the sensor portion 14, are provided in a two-dimensional form at the radiographic imaging element 12.

Plural scan lines 22, for turning the TFT switches 16 on and off, and plural signal lines 24, for reading-out the charges accumulated in the sensor portions 14, are provided at the radiographic imaging element 12 so as to intersect one another.

A scintillator 30 (see FIG. 7 and FIG. 8) formed from GOS or CsI or the like is adhered to the surface of the radiographic imaging element 12 relating to the present embodiment. In order to prevent generated light from leaking-out to the exterior, the scintillator 30 has a light-blocking body 30A (see FIG. 8) that blocks the light generated at the surface at the side opposite the adhered radiographic imaging element 12.

At the radiographic imaging element 12, radiation such as X-rays or the like that is irradiated is converted into light at the scintillator 30, and the light is illuminated onto the sensor portions 14. The sensor portions 14 receive the light illuminated from the scintillator 30, and accumulate charges.

Further, due to any of the TFT switches 16 connected to the signal line 24 being turned on, an electric signal (image signal), that expresses a radiographic image in accordance with the charge amount accumulated in the sensor portion 14, flows to the signal line 24.

Plural connectors 32 for connection are provided so as to be lined-up at one end side, in the signal line direction, of the radiographic imaging element 12. Plural connectors 34 are provided so as to be lined-up at one end side in the scan line direction. The respective signal lines 24 are connected to the connectors 32, and the respective scan lines 22 are connected to the connectors 34.

Further, a control section 36, that carries out control of radiation detection by the radiographic imaging element 12 and control of signal processing on the electric signals flowing to the respective signal lines 24, is provided in the present exemplary embodiment. The control section 36 has a signal detection circuit 42 and a scan signal control circuit 40.

Plural connectors 46 are provided at the signal detection circuit 42. Ones of ends of flexible cables 44 are electrically connected to the connectors 46. The other ends of the flexible cables 44 are connected to the connectors 32, and an amplifying circuit that amplifies the inputted electric signal is incorporated for each of the signal lines 24. In accordance with this structure, due to the electric signals inputted from the respective signal lines 24 being amplified by the amplification circuits and detected, the signal detection circuit 42 detects the charge amounts accumulated in the respective sensor portions 14, as information of the respective pixels 20 that structure the image.

On the other hand, connectors 48 are provided at the scan signal control circuit 40, and ones of ends of flexible cables 52 are electrically connected to the connectors 48. The other ends of the flexible cables 52 are connected to the connectors 34. The scan signal control circuit 40 outputs, to the respective scan lines 22, control signals for turning the TFT switches 16 on and off.

Figure 8:
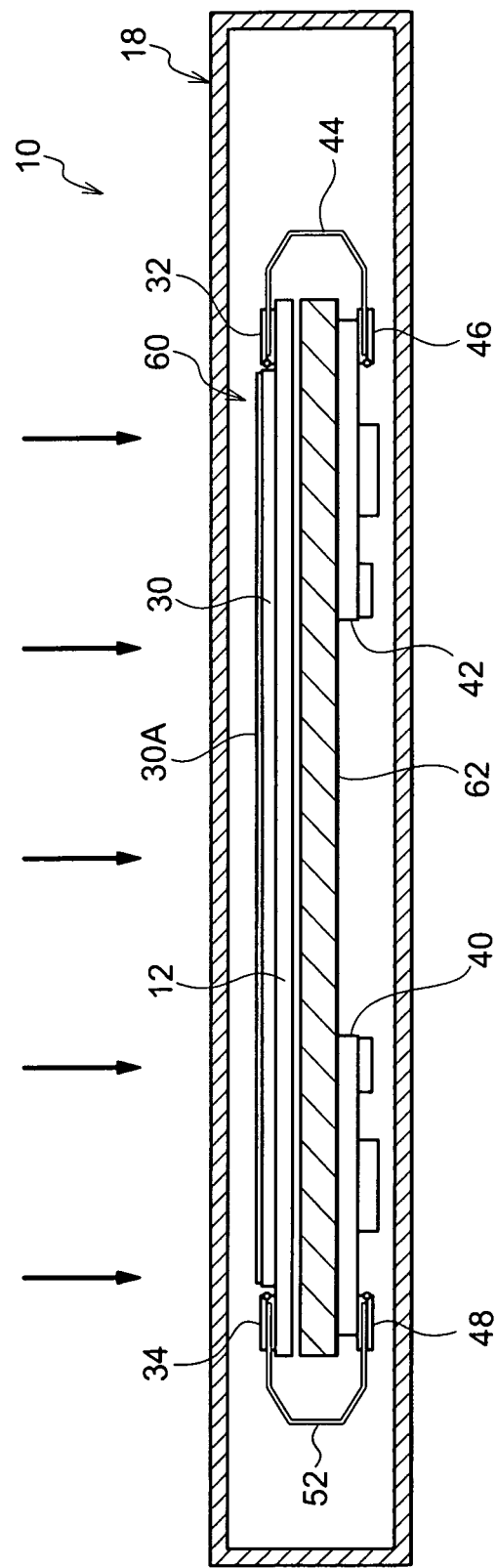
FIG. 8 is a sectional view showing the portable radiographic imaging device relating to the first exemplary embodiment of the present invention.

Further, as shown in FIG. 8, the portable radiographic imaging device 10 relating to the present exemplary embodiment has an imaging section 60 that captures the radiographic image expressed by the radiation that was irradiated. At the imaging section 60, the radiographic imaging element 12 is disposed at one surface of a supporting substrate 62 that is formed in the shape of a flat plate (see FIG. 7), and the signal detection circuit 42 and the scan signal control circuit 40, that correspond to the radiographic imaging element 12, are disposed at the other surface of the supporting substrate 62.

Further, as shown in FIG. 3, a rechargeable battery 54, that serves as a first rechargeable battery and makes the portable radiographic imaging device 10 operate, is provided at the portable radiographic imaging device 10. The rechargeable battery 54 can be freely installed in and removed from an accommodating portion 56 that is provided in a side surface of the portable radiographic imaging device 10.

Figure 2:
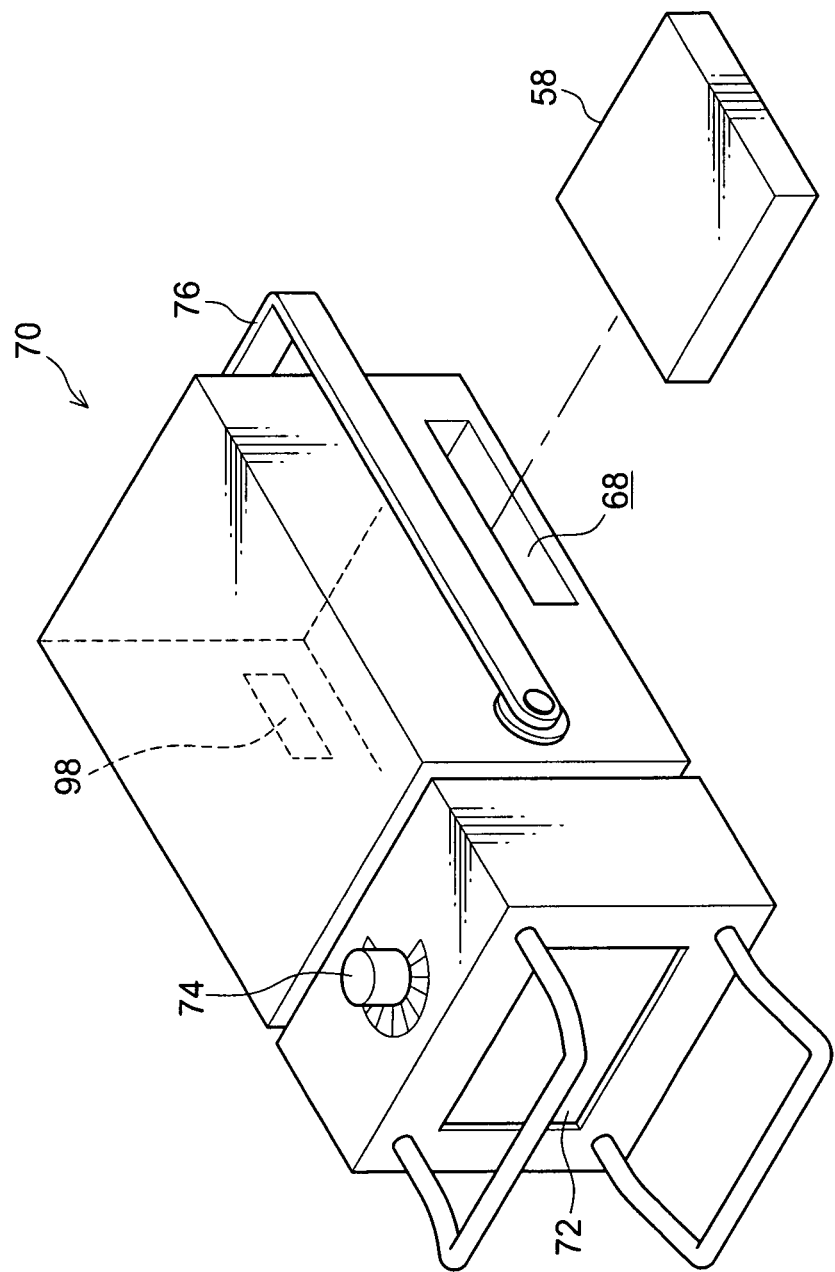
FIG. 2 is a perspective view showing a portable X-ray source used in the device system relating to the first exemplary embodiment of the present invention.

In contrast, as shown in FIG. 2, at a portable X-ray source 70 that irradiates radiation onto the portable radiographic imaging device 10, there are provided an irradiation window 72 through which X-rays are irradiated, an adjustment dial 74 that adjusts the collimator of the portable X-ray source 70, and a handle portion 76 that is grasped when carrying the portable X-ray source 70.

A rechargeable battery 58, that serves as a second rechargeable battery and makes the portable X-ray source 70 operate, is provided at the portable X-ray source 70. The rechargeable battery 58 can be freely installed in and removed from an accommodating portion 68 that is provided in a side surface of the portable X-ray source 70.

Further, as shown in FIG. 1, an accommodating case 66, in which the portable radiographic imaging device 10 and the portable X-ray source 70 can be accommodated and carried when carrying out imaging when visiting the home of an individual or a nursing facility, is provided at the device system 64 in addition to the above-described portable radiographic imaging device 10 and portable X-ray source 70. Note that details of the accommodating case 66 are described later.

Operation of the portable radiographic imaging device 10 and the portable X-ray source 70 relating to the present exemplary embodiment is described next.

Figure 5:
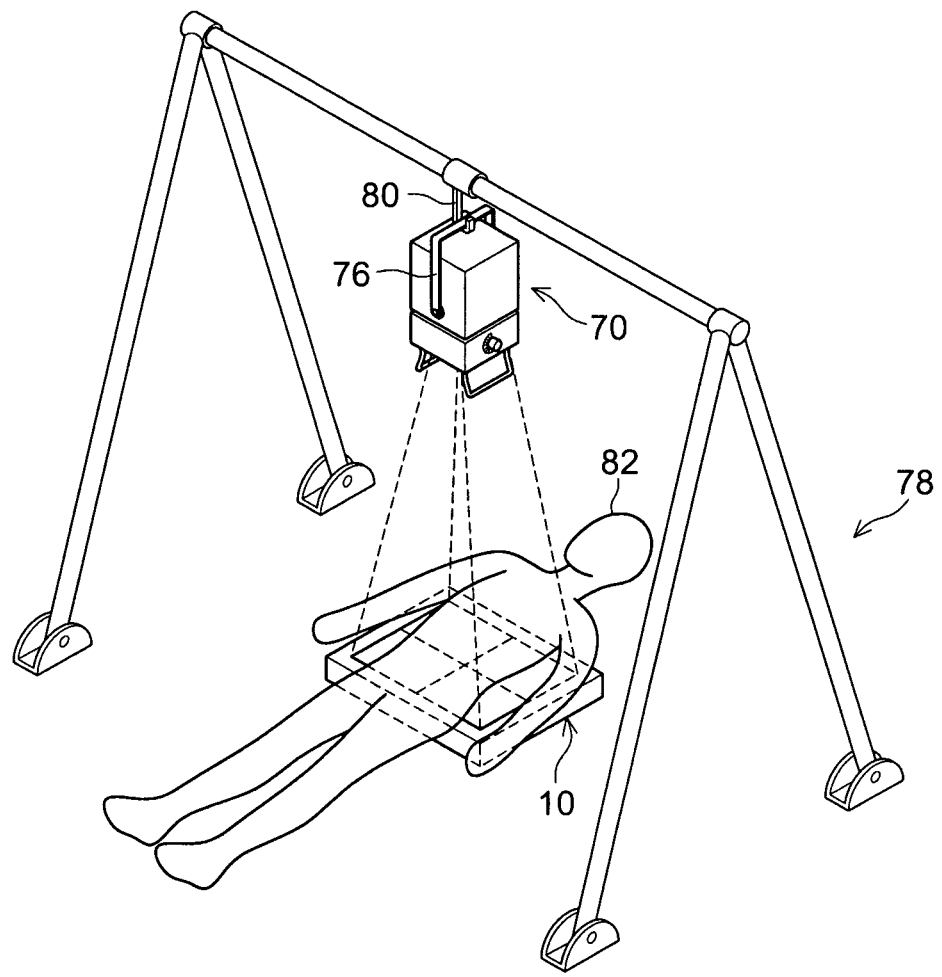
FIG. 5 is a perspective view showing a state of usage of the portable radiographic imaging device and the portable X-ray source used in the device system relating to the first exemplary embodiment of the present invention.

As shown in FIG. 5, at the time of capturing radiographic images, the portable radiographic imaging device 10, that has been accommodated in the accommodating case 66 (see FIG. 1) and carried to an individual's home or a nursing facility, is disposed with an interval between the portable radiographic imaging device 10 and the portable X-ray source 70 that generates radiation. In detail, the portable radiographic imaging device 10 and the portable X-ray source 70 are disposed with an interval in the vertical direction therebetween, by hooking the handle portion 76 of the portable X-ray source 70 on a hook portion 80 of a frame 78 that is easily assembled at the individual's home or nursing facility.

Further, the region between the portable X-ray source 70 and the portable radiographic imaging device 10 at this time is an imaging position for the positioning of a subject 82. When capturing of a radiographic image is instructed, the portable X-ray source 70 emits radiation of a radiation amount corresponding to imaging conditions and the like that are given in advance. Then, due to the radiation, that is emitted from the portable X-ray source 70, passing through the subject 82 positioned at the imaging position, the radiation carries image information, and thereafter, is irradiated onto the portable radiographic imaging device 10.

As shown in FIG. 8, at the radiographic imaging element 12, the radiation such as X-rays or the like that has been irradiated is converted into light at the scintillator 30, and the light is illuminated onto the sensor portions 14 (see FIG. 6). The sensor portions 14 receive the light illuminated from the scintillator 30, and accumulate charges.

As shown in FIG. 6, at the time of image read-out, on signals (+10 to 20 V) are successively applied from the scan signal control circuit 40 via the scan lines 22 to the gate electrodes of the TFT switches 16 of the radiographic imaging element 12. Due thereto, due to the TFT switches 16 of the radiographic imaging element 12 successively being turned on, electric signals corresponding to the charge amounts accumulated in the sensor portions 14 flow-out to the signal lines 24. On the basis of the electric signals that have flowed-out to the signal lines 24 of the radiographic imaging element 12, the signal detection circuit 42 detects the charge amounts accumulated in the respective sensor portions 14, as information of the respective pixels 20 structuring the image. Due thereto, image information, that expresses the image expressed by the radiation that was irradiated onto the radiographic imaging element 12, is obtained.

(Main Portions)

The accommodating case 66, that can accommodate and carry the portable radiographic imaging device 10 and the portable X-ray source 70, is described next.

As shown in FIG. 1, a case main body 66A, a cover portion 66B that opens the interior of the case main body 66A, a handle portion 66C that is provided at the ceiling plate of the case main body 66A and can be grasped, and driven rollers 66D that are provided at the bottom plate of the case main body 66A, are provided at the accommodating case 66.

A first accommodating portion 84, that is concave and that can accommodate the portable radiographic imaging device 10, is provided in the case main body 66A. A second accommodating portion 86, that is concave and that can accommodate the portable X-ray source 70, is provided next to the first accommodating portion 84.

A rechargeable battery 88 serving as a third rechargeable battery is provided so as to be able to be freely installed in and removed from an accommodating portion 90 that is formed in the cover portion 66B at the accommodating case 66. Further, a charging circuit 92, that serves as a charging unit that acquires electric power from the rechargeable battery 88 accommodated in the accommodating portion 90 and can charge the rechargeable batteries 54, 58 (see FIG. 2, FIG. 3) of the portable radiographic imaging device 10 and the portable X-ray source 70 that are accommodated in the accommodating case 66, is provided in the accommodating case 66.

An electricity receiving portion 94, that is provided at the portable radiographic imaging device 10 and is used at the time of charging, and an electricity supplying portion 96, that is provided at the first accommodating portion 84, do not contact one another. Similarly, an electricity receiving portion 98, that is provided at the portable X-ray source 70, and an electricity supplying portion 100, that is provided at the second accommodating portion 86, also do not contact one another.

Moreover, a power supply cable 104 that can be taken-up is provided at the cover portion 66B. By connecting this power supply cable 104 to an outlet (e.g., a wall outlet) that can supply electric power, the rechargeable battery 88 accommodated in the accommodating portion 90 is charged via a charging circuit 106 provided in the cover portion 66B.

Here, the self-discharge rate of the rechargeable battery 88 is small as compared with the rechargeable batteries 54, 58. Namely, it is difficult for the rechargeable battery 88 to discharge, as compared with the rechargeable batteries 54, 58.

The method of calculating and the method of measuring the self-discharge rate are described below.

$$\text{self-discharge rate [\%] of battery} = (\text{initial discharge capacity} - \text{discharge capacity after storage})/\text{initial discharge capacity} \times 100$$

<Measuring Method>
First Step: A single battery or a battery pack is charged at an ambient temperature of 20±5° C. by a method specified by the manufacturer.
Second Step: The single battery or battery pack is discharged, at an ambient temperature of 20±5° C., at a constant current of $0.2I_t$ [A] until the battery voltage becomes a prescribed discharge end voltage. The discharge amount at this time is the initial discharge capacity. Here, $I_t$ [A] is the hourly-rate current of the single battery or the battery pack.
Third Step: The single battery or battery pack is charged at an ambient temperature of 20±5° C. by a method specified by the manufacturer.
Fourth Step: The single battery or battery pack is left for 28 days in an ambient temperature of 20±5° C.
Fifth Step: The single battery or battery pack is discharged, at an ambient temperature of 20±5° C., at a constant current of $0.2I_t$ [A] until the battery voltage becomes a prescribed discharge end voltage. The discharge amount at this time is the discharge capacity after storage.

(Operation/Effects)

The operation of the accommodating case 66 and the device system 64 is described next.

As shown in FIG. 1, when, due to imaging being carried out during a visit to an individual's home or a visit to a nursing facility or the like, the portable radiographic imaging device 10 and the portable X-ray source 70 are to be brought to the destination of the visit and used thereat, the portable radiographic imaging device 10 and the portable X-ray source 70 are accommodated in the first accommodating portion 84 and the second accommodating portion 86 of the accommodating case 66. Note that the rechargeable battery 88, that is accommodated in the accommodating portion 90 of the cover portion 66B, is charged in advance by using the power source cable 104 and the charging circuit 106.

As shown in FIG. 4A, the cover portion 66B of the accommodating case 66 is closed, the handle portion 66C is grasped, the accommodating case 66 is conveyed while the driven rollers 66D are rolled, and the portable radiographic imaging device 10 and the portable X-ray source 70 are carried to an individual's home or a nursing facility.

When the charged amount of the rechargeable battery 54 accommodated in the portable radiographic imaging device 10 or the rechargeable battery 58 accommodated in the portable X-ray source 70 is low, or when there are several destinations to visit and the charged amount of the battery 54, 58 has become low, the rechargeable battery 54, 58 must first be charged when arriving at the individual's home or the nursing facility. If the rechargeable battery 54, 58 is not charged, imaging may not be able to be carried out immediately after arriving.

However, as shown in FIG. 1, in the present invention, the charging circuit 92 provided in the accommodating case 66 acquires electric power from the rechargeable battery 88, and charges the rechargeable battery 54 of the portable radiographic imaging device 10 and the rechargeable battery 58 of the portable X-ray source 70 that are accommodated. Namely, the portable radiographic imaging device 10 and the portable X-ray source 70 are accommodated in the accommodating case 66, and the rechargeable batteries 54, 58 are charged during transport.

Further, as shown in FIG. 4B, while using the portable radiographic imaging device 10 and the portable X-ray source 70 when an individual's home or a nursing facility or the like has been reached, the rechargeable battery 88 accommodated in the cover portion 66B is charged by inserting the power source cable 104 into an outlet.

As described above, by providing the charging circuit 92 at the accommodating case 66, the rechargeable batteries 54, 58 can be charged in a state in which the portable radiographic imaging device 10 and the portable X-ray source 70 are accommodated and transported in the accommodating case 66 that is portable.

Further, the rechargeable battery 88, from which the charging circuit 92 acquires electric power, is provided at the accommodating case 66. Due thereto, the rechargeable batteries 54, 58 of the portable radiographic imaging device 10 and the portable X-ray source 70 that are being transported can be charged by a simple structure.

Moreover, the power source cable 104, that makes it possible to charge the rechargeable battery 88 by electric power from the exterior, is provided at the accommodating case 66. Due thereto, at the destination of a visit or within a hospital, the rechargeable battery 88 can be charged by connecting the power source cable 104 to an outlet (e.g., a wall outlet) that can supply electric power.

Further, if the portable radiographic imaging device 10 and the portable X-ray source 70 are to be charged individually, cables provided at the portable radiographic imaging device 10 and the portable X-ray source 70 respectively must be connected to outlets that can supply electric power, and there may not be a sufficient number of insertion ports of the outlet. However, in the present exemplary embodiment, the rechargeable battery 88, that is used to charge the rechargeable batteries 54, 58, can be charged by inserting the power source cable 104, that is provided at the accommodating case 66, into an outlet. Therefore, the number of insertion ports of the outlet is not insufficient.

Moreover, the insertion shapes of outlets differ in accordance with the country or geographical region, and differ also in accordance with the means of transport (planes, boats, automobiles and the like). Thus, if cables for charging are provided respectively at the portable radiographic imaging device 10 and the portable X-ray source 70, cables suited to respective specifications are needed for both (in this case, two cables×countries or geographical regions, or means of transport). However, in the present exemplary embodiment, because the power source cable 104 is provided at the accommodating case 66, the rechargeable battery 88 can be charged by making only the power source cable 104 suit the respective specifications (one cable×countries or geographical regions, or means of transport).

Further, the self-discharge rate of the rechargeable battery 88 is low as compared with the rechargeable batteries 54, 58. Namely, it is difficult for the rechargeable battery 88 to discharge, as compared with the rechargeable batteries 54, 58. Therefore, the rechargeable battery 88 is accommodated in the accommodating case 66, and, when charging the rechargeable batteries 54, 58 by using the rechargeable battery 88, the rechargeable batteries 54, 58 can be charged effectively.

Moreover, the rechargeable battery 88 is provided so as to be able to be installed in and removed from the accommodating case 66. Therefore, while the portable radiographic imaging device 10 and the portable X-ray source 70 are accommodated in the accommodating case 66 and transported, when the charged amount of the rechargeable battery 88 becomes low, the rechargeable batteries 54, 58 can be charged by replacing the installed rechargeable battery 88 with a charged rechargeable battery 88 that has been readied in advance.

Still further, the electricity receiving portion 94 of the portable radiographic imaging device 10 and the electricity supplying portion 96 provided at the first accommodating portion 84 do not contact one another, and the electricity receiving portion 98 of the portable X-ray source 70 and the electricity supplying portion 100 provided at the second accommodating portion 86 do not contact one another. Therefore, the waterproofness and the appearance of the portable radiographic imaging device 10 and the portable X-ray source 70 can be improved.

Note that, although the present invention has been described in detail with reference to a specific exemplary embodiment, the present invention is not limited to this embodiment, and it will be clear to those skilled in the art that various other embodiments are possible within the scope of the present invention. For example, although the portable radiographic imaging device 10 and the portable X-ray source 70 are accommodated in the accommodating case 66 in the above-described exemplary embodiment, it is possible to accommodate either one thereof.

Further, in the above exemplary embodiment, although not described in particular, a personal computer, such as a notebook type or the like, that controls the portable radiographic imaging device 10 and the portable X-ray source 70 may be used when images of the subject 82 are captured by using the portable radiographic imaging device 10 and the portable X-ray source 70.

Examples of an accommodating case 122 and a device system 120 relating to a second exemplary embodiment of the present invention are described next in accordance with FIG. 9 and FIG. 10. Note that members that are the same as in the first exemplary embodiment are denoted by the same reference numerals, and description thereof is omitted.

Figure 10:
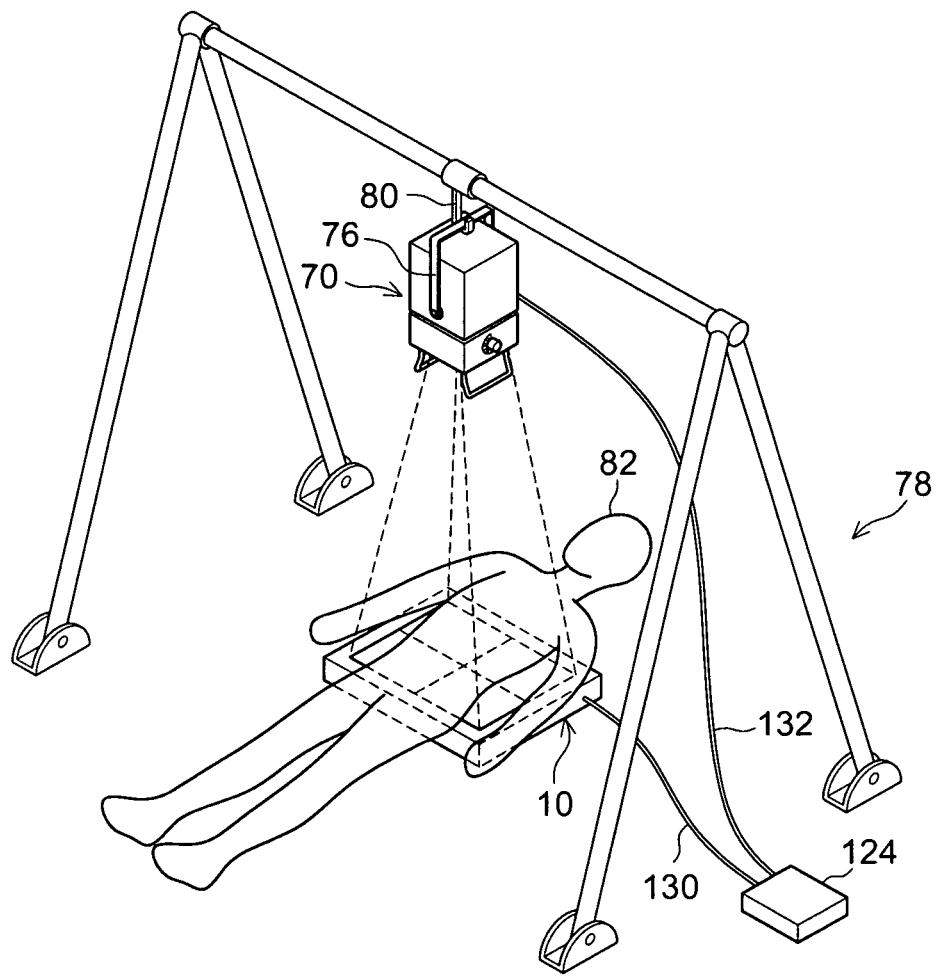
FIG. 10 is a perspective view showing a state of usage of the portable radiographic imaging device and the portable X-ray source used in the device system relating to the second exemplary embodiment of the present invention.

As shown in FIG. 10, a rechargeable battery 124, that makes the portable radiographic imaging device 10 and the portable X-ray source 70 operate, is not accommodated in the portable radiographic imaging device 10 and the portable X-ray source 70, and is provided separately from the portable radiographic imaging device 10 and the portable X-ray source 70.

Further, when using the portable radiographic imaging device 10 and the portable X-ray source 70, electric power is supplied to the portable radiographic imaging device 10 and the portable X-ray source 70 by connecting the rechargeable battery 124, and the portable radiographic imaging device 10 and the portable X-ray source 70, by cables 130, 132.

Figure 9:
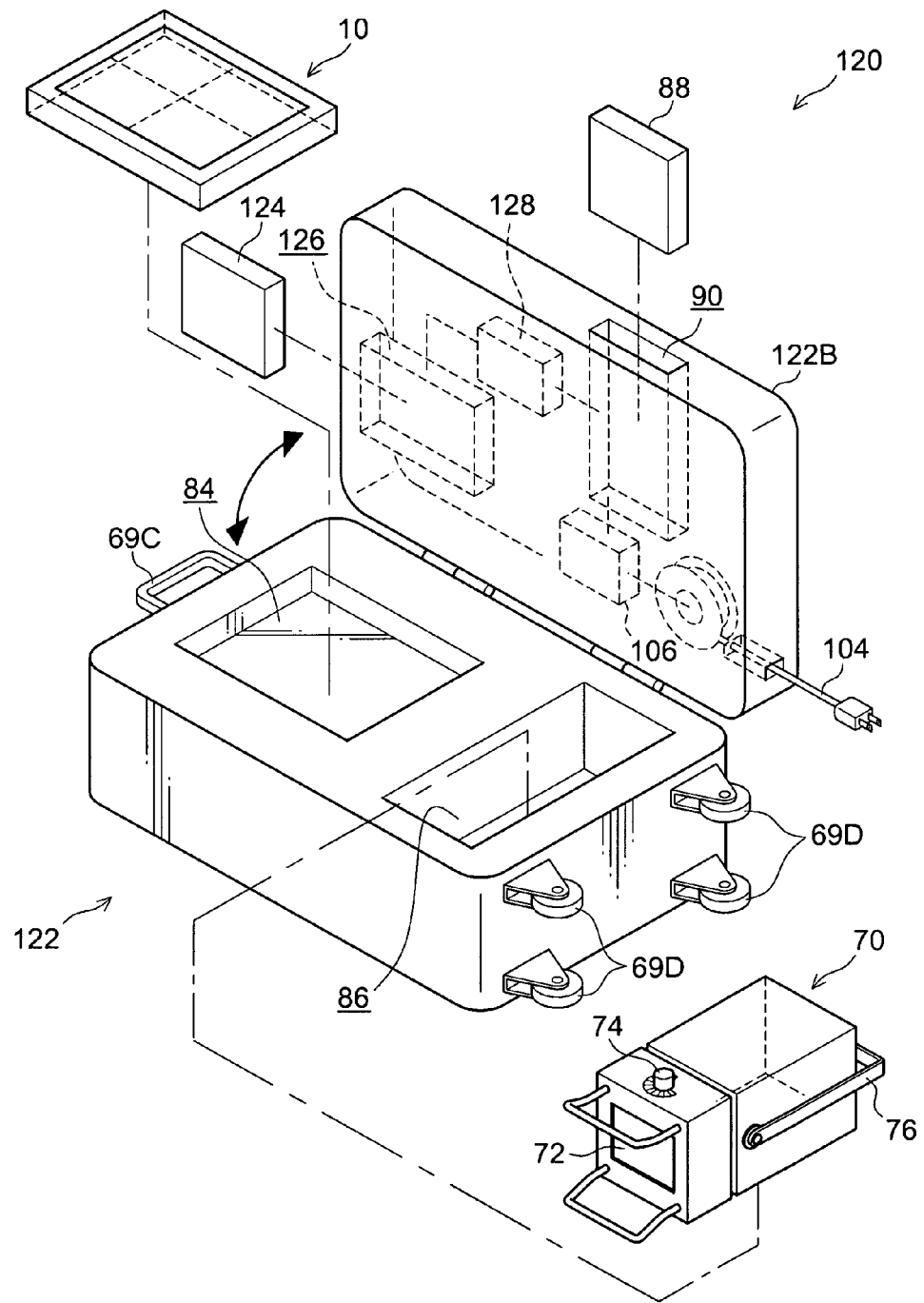
FIG. 9 is a perspective view showing an accommodating case and a device system relating to a second exemplary embodiment of the present invention.

Moreover, as shown in FIG. 9, an accommodating portion 126, that accommodates the rechargeable battery 124 such that the rechargeable battery 124 can be freely installed therein and removed therefrom, is provided in a cover portion 122B of the accommodating case 122 that structures the device system 120. Still further, a charging circuit 128 serving as a charging unit is provided at the cover portion 122B. The charging circuit 128 acquires electric power from the rechargeable battery 88 accommodated in the accommodating portion 90, and charges the rechargeable battery 124 that is accommodated in the accommodating portion 126.

What is claimed is:

1. An accommodating case that is portable, comprising:
an accommodating section that can accommodate at least one of a portable radiographic imaging device, that records radiographic images expressed by irradiated radiation and that operates due to a first rechargeable battery, and or a portable X-ray source, that irradiates radiation toward the portable radiographic imaging device and operates due to a second rechargeable battery;
a charging unit that acquires electric power from an electric power supplying source, and can charge at least one of the first rechargeable battery and the second rechargeable battery; and,
a cover portion that covers the at least one of the portable radiographic imaging device or the portable X-ray source housed in the accommodating section in the case that the accommodating case is being conveyed, and closes the accommodating section,
wherein the accommodating section is configured such that the at least one of a portable radiographic imaging device or a portable X-ray source can be taken out therefrom when being used.

2. The accommodating case of claim 1, wherein the electric power supplying source is a third rechargeable battery provided in the accommodating case, and a power source cable, that can charge the third rechargeable battery by electric power from an exterior, is provided.

3. The accommodating case of claim 2, wherein a self-discharge rate of the third rechargeable battery is small as compared with the first rechargeable battery and the second rechargeable battery.

4. The accommodating case of claim 2, wherein the third rechargeable battery is provided so as to be able to be installed and removed.

5. The accommodating case of claim 1, wherein electricity receiving portions of the portable radiographic imaging device and the portable X-ray source accommodated in the accommodating section, and electricity supplying portions provided at the accommodating section, do not contact one another.

6. A device system comprising:
an accommodating case that is portable, comprising:
an accommodating section that can accommodate at least one of a portable radiographic imaging device, that records radiographic images expressed by irradiated radiation and that operates due to a first rechargeable battery, or a portable X-ray source, that irradiates radiation toward the portable radiographic imaging device and operates due to a second rechargeable battery;

a charging unit that acquires electric power from an electric power supplying source, and can charge at least one of the first rechargeable battery and the second rechargeable battery; and, a cover portion that covers the at least one of the portable radiographic imaging device or the portable X-ray source housed in the accommodating section in the case that the accommodating case is being conveyed, and closes the accommodating section;

wherein the at least one of a portable radiographic imaging device or a portable X-ray source is accommodated in the accommodating section provided at the accommodating case;

wherein the accommodating section is configured such that the at least one of a portable radiographic imaging device or a portable X-ray source can be taken out therefrom when being used.

* * * * *